United States Patent [19]
Schröter

[11] 3,974,284
[45] Aug. 10, 1976

[54] 1,1a,6,10b-TETRAHYDRO-1,6-METHANO-DIBENZO[a,e]CYCLOPROPA[c]CYCLO-HEPTENES AS ANTIDEPRESSANTS AND STIMULANTS

[75] Inventor: Herbert Schröter, Fullinsdorf, Switzerland

[73] Assignee: Ciba-Geigy Corporation, Ardsley, N.Y.

[22] Filed: Dec. 6, 1974

[21] Appl. No.: 530,115

Related U.S. Application Data

[62] Division of Ser. No. 376,670, July 5, 1973, Pat. No. 3,883,537.

[30] Foreign Application Priority Data

July 7, 1972 Switzerland............... 10215/72

[52] U.S. Cl................................ 424/267; 424/330
[51] Int. Cl.$^2$........................................ A61K 9/22
[58] Field of Search........................... 424/267, 330

[56] References Cited
UNITED STATES PATENTS
3,883,537   5/1975   Schröter ............... 260/293.62

OTHER PUBLICATIONS
Cioranescu et al., Rev. Roum. Chim. 14 (7), pp. 911–27 (1969).
Cristol et al., J. Am. Chem. Soc. 90 (20), pp. 5564–5571 (1968).
Ioan et al., Tetrahedron Letters 38, pp. 3383–3386 (1965).

*Primary Examiner*—G. Thomas Todd
*Attorney, Agent, or Firm*—Joseph G. Kolodny; John J. Maitner; Theodore O. Groeger

[57] ABSTRACT

Compounds of the class of 1,1a,6,10b-tetrahydro-1,6-methano-dibenzo[a,e]cyclopropa[c]cycloheptene derivatives and their pharmaceutically acceptable acid addition salts have valuable pharmacological properties and are active ingredients for therapeutic compositions. In particular, these new compounds have an antidepressive and stimulating action. Specific embodiments are N-methyl-1,1a,6,10b-tetrahydro-1,6-methano-dibenzo[a,e]cyclopropa[c]cycloheptene-11-amine-hydrochloride, N,N-dimethyl-1,1a,6,10b-tetrahydro-1,6-methano-dibenzo[a,e]cyclopropa[c]cycloheptene-11-amine-fumarate,N-methyl-1,1a,6,10b-tetrahydro-1,6-methano-dibenzo[a,e]cyclopropa[c]cycloheptene-11-methylamine-maleate, N,N-dimethyl-1,1a,6,10b-tetrahydro-1,6-methano-dibenzo[a,e]cyclopropa[c]cycloheptene-11-methylamine-hydrochloride,N,N-dimethyl-11-hydroxy-1,1a,6,10b-tetrahydro-1,6-methano-dibenzo[a,e]cyclopropa[c]cycloheptene-11-methylamine-fumarate and N,N-dimethyl-11-hydroxy-1,1a,6,10b-tetrahydro-1,6-methano-dibenzo[a,e]cyclopropa[c]cycloheptene-11-ethylamine-hydrochloride.

5 Claims, No Drawings

1,1a,6,10b-TETRAHYDRO-1,6-METHANO-DIBENZO[a,e]CYCLOROPA[c]CYCLOHEPTENES AS ANTIDEPRESSANTS AND STIMULANTS

This is a division of application Ser. No. 376,670, filed July 5, 1973, now U.S. Pat. No. 3,883,537.

The present invention relates to new 1,1a,6,10b-tetrahydro-1,6-methano-dibenzo[a,e]cyclopropa[c]cycloheptene derivatives, to processes for their production, to therapeutic preparations containing the new compounds, and to the use thereof.

The compounds according to the invention correspond to the general formula I

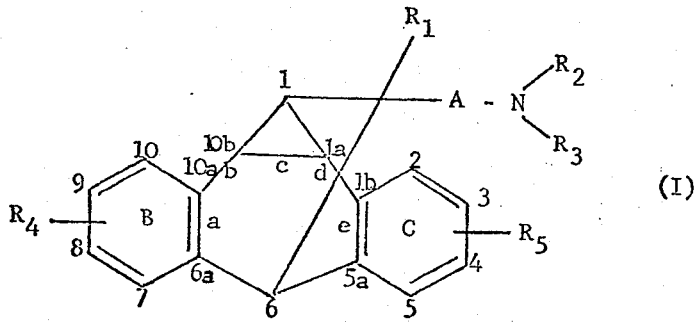

(I)

wherein
R₁ represents hydrogen or the hydroxy group,
R₂ and R₃ represent hydrogen, or alkyl groups having 1 to 3 carbon atoms,
R₄ and R₅ represent hydrogen, halogen up to atomic number 35, trifluoromethyl, alkyl or alkoxy groups having 1 to 3 carbon atoms, hydroxy groups which can optionally be esterified, and
A represents the direct bond, an alkylene radical having 1 to 3 carbon atoms, or together with

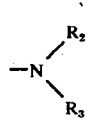

the 1-methyl-4-piperidyl radical.

The invention also relates to the addition salts of the compounds of the general formula I with inorganic and organic acids.

As alkyl groups having 1 to 3 carbon atoms in compounds of the general formula I, R₂ and R₃ are, for example, ethyl, propyl or isopropyl groups, but preferably methyl groups.

Halogen atoms as substituents R₄ and R₅ are fluorine, chlorine or bromine atoms. The ethoxy, propoxy, isopropyloxy and, preferably, the methoxy group are mentioned as alkoxy groups R₄ and R₅ having 1 to 3 carbon atoms.

Esterified hydroxy groups R₄ and R₅ are, for example, those which are esterified with an aliphatic carboxylic acid having 2 to 20 carbon atoms; to be mentioned in particular are acetic acid, propionic acid, n-butyric acid, n-hexanecarboxylic acid, n-heptanecarboxylic acid, n-decanecarboxylic acid, palmitic acid, oleic acid and stearic acid. Further carboxylic acids applicable are such which are derived from phenylcarboxylic acids, optionally from those having one or more alkoxy substituents, such as, for example, benzoic acid, p-ethoxybenzoic acid and, in particular, 3,4,5-trimethoxybenzoic acid.

As an alkylene radical having 1 to 3 carbon atoms, A represents the methylene, ethylene, propylene and trimethylene radical.

Of the substituents, R₅ is especially in the 3- or 4-position and represents, besides hydrogen, also fluorine, bromine, the trifluoromethyl group, an alkyl group, an alkoxy or hydroxy group, or an esterified hydroxy group, particularly however chlorine. A preferred class of compounds of the general formula I is the class in which both R₄ and R₅ stand for hydrogen; a further preferred group of compounds of this type is the group in which R₅ represents chlorine, or an alkoxy group having 1 to 3 carbon atoms, whereby R₄ is then hydrogen. A further group of compounds of the general formula I of particular interest are the compounds in which R₅ has the aforementioned special substituent-meanings, and R₄ represents fluorine, bromine, chlorine, trifluoromethyl or an alkoxy group in any desired position, especially however, chlorine or an alkoxy group in the 9-position, and A represents the direct bond, the methylene or ethylene radical, or together with NR₂R₃ the 1-methyl-4-piperidyl radical.

The compounds of the general formula I and the corresponding addition salts with inorganic and organic acids possess valuable pharmacological properties. They have an antidepressive and stimulating action. The antidepressive action can be established, for example, by determination of the reserpine-antagonistic activity in the reserpine-ptosis test on the mouse and on the rat with doses of from ca. 10 mg/kg i.p., and also by an examination of the tetrabenazine-antagonistic activity on the rat with doses of 20 to ca. 40 mg/kg i.p.. The central-stimulating properties, especially the antidepressive properties, which can be determined by selected standard tests [cp. R. Domenjoz and W. Theobald, Arch.Int.Pharmacodyn. 120, 450 (1959), as well as W. Theobald et al., Arzneimittelforsch. 17, 561 (1967)], distinguish the compounds of the general formula I and their pharmaceutically acceptable addition salts with inorganic and organic acids as active substances for antidepressants and central stimulants, which are used, for example, for the treatment of depressive psychosis and also of masked and endogenous depressions.

Of particular importance are compounds of the general formula I wherein R₁ is hydrogen or hydroxyl, R₂ and R₃ represent hydrogen and/or methyl or ethyl groups, R₅ is hydrogen or a halogen atom up to atomic number 35, trifluoromethyl, an alkoxy or hydroxy group or an esterified hydroxy group, and $R_4$ represents either hydrogen or one of the stated substituents, and A is the direct bond, the methylene, ethylene or 1-methyl-4-piperidyl radical. Compounds especially valuable within this group are compounds are those in which $R_1$ represents hydrogen or hydroxyl, $R_2$ and $R_3$ represent hydrogen and/or methyl groups, $R_4$ and $R_5$ hydrogen, and A has the aforementioned specific meanings. Such compounds which combine the given substitution characteristics are:

1,1a,6,10b-tetrahydro-1,6-methano-dibenzo[a,e]cyclopropa[c]cycloheptene-11-amine,
N-methyl-1,1a,6,10b-tetrahydro-1,6-methano-dibenzo[a,e]cyclopropa[c]cycloheptene-11-amine,
N,N-dimethyl-1,1a,6,10b-tetrahydro-1,6-methano-dibenzo[a,e]cyclopropy[c]cycloheptene-11-amine,
N-methyl-1,1a,6,10b-tetrahydro-1,6-methano-dibenzo[a,e]cyclopropa[c]cycloheptene-11-methylamine,
N,N-dimethyl-1,1a,6,10b-tetrahydro-1,6-methano-dibenzo[a,e]cyclopropa[c]cycloheptene-11-methylamine,
N,N-dimethyl-11-hydroxy-1,1a,6,10b-tetrahydro-1,6-methano-dibenzo[a,e]cyclopropa[c]cycloheptene-11-methylamine,
N,N-dimethyl-11-hydroxy-1,1a,6,10b-tetrahydro-1,6-methano-dibenzo[a,e]cyclopropa[c]cycloheptene-11-ethylamine,
N-isopropyl-11-hydroxy-1,1a,6,10b-tetrahydro-1,6-methano-dibenzo[a,e]cyclopropa[c]cycloheptene-11-methylamine, as well as 4-(11-hydroxy-1,1a,6,10b-tetrahydro-1,6-methano-dibenzo[a,e]cyclopropa[c]cyclohepten-11-y)-1-methylpiperidine.

A further group of specially valuable compounds are, on the one hand, those which are derived from the above listed and defined compounds in which $R_1$ is hydrogen, in that ring B either remains unsubstituted or, preferably, carried in the 9-position a halogen atom, particularly chlorine or a methoxy group, and ring C carries, as substituent $R_5$, and esterified hydroxy group of which the ester component is preferably acetic acid, propionic acid, n-butyric acid, n-hexanoic acid, n-decanoic acid or palmitic acid; and, on the other hand, substances in which ring C is unsubstituted or, preferably, carries in the 3- or 4-position a halogen atom, particularly chlorine or a methoxy group, while in ring B there is, as substituent $R_4$, and esterified hydroxy group of the aforementioned type.

A further group of substances of particular interest are those which differ from the compounds defined in the foregoing by a chlorine atom or a methoxy group, on the one hand in the 3- or 4-position or, on the other hand, in the 9-position, whereby $R_1$ can be either hydrogen or the hydroxy group.

The compounds of the general formula I and their acid addition salts are produced according to the invention by the reaction of a compound of the general formula II

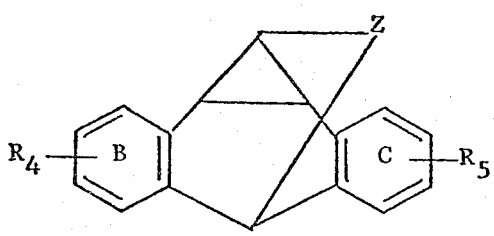

(II)

wherein
$R_4$ and $R_5$ have the meanings given under formula I, and
Z represents the carbonyl group or the radical

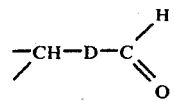

wherein
D stands for the direct bond, the methylene, ethylene or ethylidene radical,
with a compound of the general formula III

wherein $R_2$ and $R_3$ have the meanings given under formula I, or with hydroxylamine; the reduction of the reaction mixture; and, optionally, the conversion of a thus obtained reaction product of the general formula I wherein $R_2$ and/or $R_3$ is hydrogen into a reaction product of the general formula I wherein $R_2$ and $R_3$ represent the alkyl groups defined there.

This process is carried out, for example, by reaction of a compound of the general formula II with a compound of the general formula III in an inert solvent such as, e.g. methanol, ethanol, isopropanol or tetrahydrofuran, or mixtures thereof, at room temperature or preferably at between 20° and 80°C. The reaction product can be obtained in the process as a precipitate, which according to the invention is subsequently reduced to an amine of the general formula I. The reduction of the enamine is however advantageously performed with the whole reaction mixture with the use of a complex metal hydride such as, for example, lithium aluminium hydride, also dihydro-[bis-(2-methoxy)-ethoxy]-sodium aluminate and tri-tert.-butyloxyaluminium hydride or sodium boron hydride, whereby the use of sodium boron hydride is given preference. A further advantageous embodiment of the process according to the invention is the catalytic reduction in the presence of Raney nickel, and particularly of noble-metal catalysts such as, for instance, palladium charcoal catalysts or platinum oxide. Depending on the nature of the employed compounds of the general formula III, compounds are obtained in this manner, wherein $R_2$ and/or $R_3$ represent(s) hydrogen, of which the conversion into compounds of the general formula I wherein $R_2$ and/or $R_3$ represent(s) alkyl groups is effected by subsequent alkylation. This is carried out for example by the reaction of an oxo compound having 1 to 3 carbon atoms with a compound of the general formula I of the given type, and the reduction in situ of the reaction product, A third process according to the invention for the production of compounds of the general formula I whereby $R_1$ is the hydroxy group comprises the reaction of a compound of the general formula V

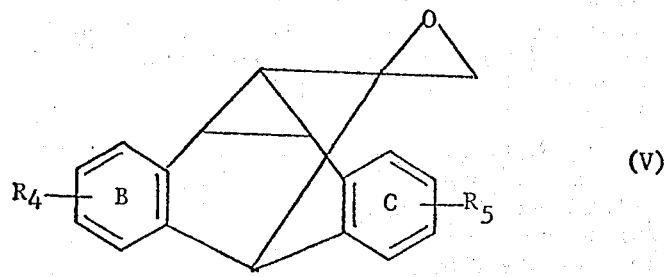

(V)

whereby the reducing agent used is advantageously formic acid at the boiling point of the reaction mixture. The subsequent introduction of alkyl radicals can, however, also be effected by reaction with a reactive ester of a corresponding alkanol, optionally in the presence or absence of a further basic condensing agent such as, for example, sodium carbonate, potassium carbonate, triethylamine or N-ethyl-N,N-diisopropylamine. Suitable reactive esters of corresponding alkanols are, e.g., the chlorides, particularly also the bromides and iodides, but also the esters with sulphuric acid, methanesulphonic acid, o- and p-toluenesulphonic acid as well as o- and p-chlorobenzenesulphonic acid.

A second process according to the invention for the production of compounds of the general formula I comprises the reduction of a compound of the general formula IV

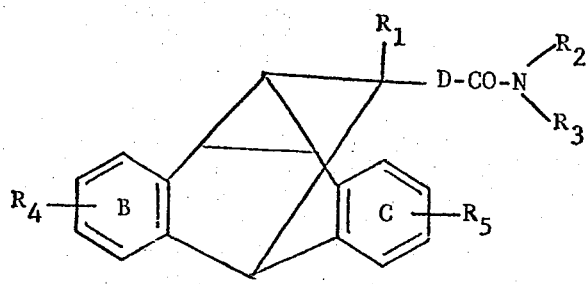

(IV)

wherein $R_1$, $R_2$, $R_3$, $R_4$ and $R_5$ have the meanings given under formula I, and D has the meaning given under formula II. In the reaction according to the process, the carbonyl group is reduced to the corresponding methylene radical. This process is performed by the use of a complex metal hydride such as, e.g. lithium aluminium hydride, or diborane, whereby there is used as the reaction medium an inert solvent such as, e.g. ether, dioxane or tetrahydrofuran, or mixtures thereof. The reduction is performed at room temperature, or preferably, however, at between 20° and 80°C.

If in this manner there is obtained a compound of the general formula I wherein $R_2$ and/or $R_3$ is (are) hydrogen, then such a compound can optionally be converted by a subsequent alkylation, already described in the case of the first process, into a compound of the general formula I in which $R_2$ and $R_3$ represent an alkyl group of the defined type.

wherein $R_4$ and $R_5$ have the meanings given under formula I with a compound of the previously described general formula III. The aminolysis on which the reaction is based is advantageously performed in an inert organic solvent such as, e.g. in a lower alkanol such as, for instance, methanol, ethanol, propanol or isopropanol, or, for example, in dioxane or tetrahydrofuran, or mixtures thereof with lower alkanols, at room temperature or at a temperature of ca. 20° to 80°C. If in this manner there is obtained a compound embraced by the general formula I wherein $R_2$ and/or $R_3$ stand(s) for hydrogen, then the subsequent introduction of 1 or 2 alkyl radicals can afterwards be effected in the manner described in connection with the first process, with the corresponding respective meanings for $R_2$ and $R_3$.

A fourth process according to the invention for the production of compounds of the general formula I wherein $R_1$ is the hydroxy group comprises the reaction of a compound of the previously described general formula II wherein Z represents the carbonyl group with 1-methyl-4-chloropiperidine, or with a 3-dialkylaminopropyl chloride in which the alkyl radicals can be either identical or different and contain 1 to 3 carbon atoms. The reaction is performed according to Grignard, preferably by means of magnesium chips in an inert solvent and in a temperature range of from 20° to 80°C, preferably at 60°C. Suitable inert solvents to be used in the anhydrous state are, e.g. diethyl ether, diisopropyl ether, di-n-butyl ether, dioxane, and particularly tetrahydrofuran.

A fifth process according to the invention for the production of compounds of the general formula I comprises the reaction of a reactive ester of a compound of the general formula VI

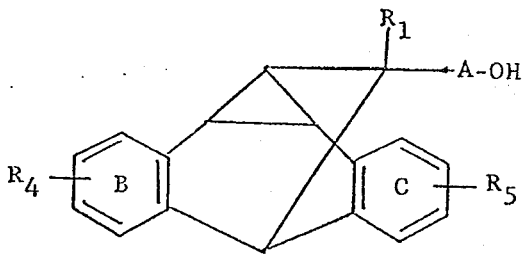

(VI), wherein $R_1$, $R_4$, $R_5$ and A have the meanings defined under formula I, with a compound of the previously described formula III, or with hexamethylenetetramine. In this reaction, the reactive ester group is exchanged direct for the amino group of the stated type, while the reaction product is converted with hexamethylenetetramine by subsequent decomposition with a diluted mineral acid, e.g., hydrochloric acid, into a compound of the general formula I. Reactive esters in the stated sense are, for example, the halides, for instance the chlorides, and particularly the bromides, and especially the iodides produced from these in situ immediately before the reaction; also suitable are the esters with methanesulphonic acid, o- and p-toluenesulphonic acid, or o- and p-chlorobenzenesulphonic acid. The reaction media used are lower alkanols, e.g. methanol, ethanol, propanol, isopropanol and butanol; advantageously, it is however also possible to use lower fatty acid amides such as, e.g. dimethylformamide or mono- and dimethylacetamide, also acetonitrile or sulpholane, or mixtures of the stated solvents. The reaction may be performed at room temperature, advantageously, however, within a temperature range of 20° to 150°C, whereby the rate of reaction is to an evident degree dependent on the nature of the employed amine of formula III on the one hand, and on the other hand on the solvent used and the reaction temperature. The reaction of a reactive ester of the general formula VI, preferably of the chloride or bromide, with hexamethylenetetramine is performed in an inert solvent, e.g. methylene chloride, chloroform, chlorobenzene, or mixtures thereof, at room temperature, or in a temperature range of 20° to 40°C, with a standing time of several hours. This is followed by decomposition of the reaction product with, for example, dilute hydrochloric acid to obtain a compound of the general formula I wherein $R_2$ and $R_3$ represent hydrogen.

If in this manner there is obtained a compound of the general formula I wherein $R_2$ and/or $R_3$ represent(s) hydrogen, then the subsequent introduction of 1 or 2 alkyl radicals can be effected in a manner corresponding to that described in the case of the first process.

A sixth process according to the invention comprises the reaction of a compound of the previously described general formula II wherein Z represents the radical

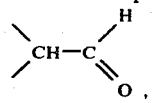

and $R_4$ and $R_5$ have the meanings given under formula I, with vinyl methyl ether, whereby there is formed an intermediate of the general formula VII

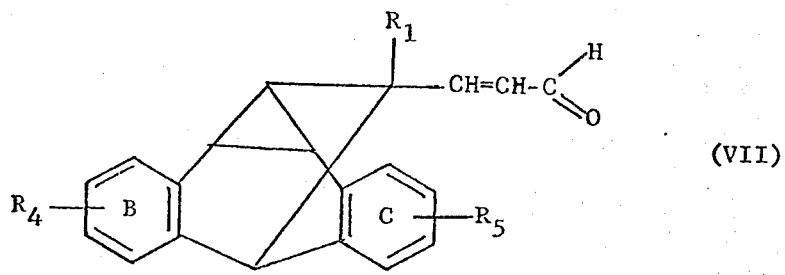

(VII)

wherein $R_1$ is hydrogen, and $R_4$ and $R_5$ have the defined meanings. The reaction is carried out in the presence of a Lewis acid; the one preferably used is boron trifluoride, or this in the form of its addition compounds, e.g. the etherates. An inert solvent is employed as the reaction medium, such as, e.g. diethyl ether, diisopropyl ether, di-n-butyl ether, dioxane, tetrahydrofuran, also aromatic hydrocarbons such as, e.g. benzene or toluene, or mixtures of such solvents, with the reaction temperature being within a range of −25° to 150°C, preferably between 20° and 40°C. The obtained reaction solution may be used as such for the subsequent reaction with a compound of the previously described general formula III or with hydroxylamine; advantageously, however, the solvents are removed beforehand under mild conditions, i.e. in vacuo at a temperature not exceeding 40°C.

The reaction with a compound of the general formula III or with hydroxylamine is performed in the manner described in the case of the first process, whereby there is formed in the reaction mixture an unsaturated product having 2 double bonds, of which the one is to be attributed to the enamine structure of the reaction product, while the other is an ethylene double bond. For the conversion of such a reaction product into a compound of the general formula I there follows according to the invention a reduction which is performed with hydrogen in the presence of catalysts, particularly noble-metal catalysts such as, e.g. palladium-charcoal or platinum oxide, in an inert solvent such as, e.g. in a lower alkanol, dioxane or tetrahydrofuran. As a reducing agent it is also possible to use zinc in dilute mineral acids. In the case of this reduction, both double bonds are hydrogenated, and a final product of the type characterised by the general formula I is obtained.

The reduction can, however, be performed in steps in such a manner that, for example, the enamine double bond is converted into a single bond with the aid of a complex metal hydride, such as lithium aluminium hydride or sodium borohydride, in an inert solvent, while the ethylene double bond remains and is reduced in the following stage by catalytic processes with hydrogen, or, e.g., zinc in diluted mineral acids. If in a compound of the general formula I obtained in this manner, the radicals $R_2$ and/or $R_3$ represent hydrogen, then a subsequent alkylation can be performed as described in connection with the first process.

Starting materials for the first-mentioned process of the general formula II wherein Z represents the carbonyl group are in some cases known from the literature [cp. V. Ioan, M. Popovici et al: Tetrahedron Letters 38, 3383–3386 (1965)]. The compound of formula II substituted, corresponding to the meaning of $R_5$, in the 4-position by chlorine is accessible from the 3-chloro-5H-dibenzo[a,d]cycloheptene-5-carbonitrile described in the literature (cp. French Patent Specification No. 1,355,829), the corresponding carboxylic acid obtainable from this and the carboxylic acid chloride to be produced therefrom, from which are producible, by cyclisation, starting materials of the type characterised by the general formula II. It is possible to produce in an analogous manner the compounds of formula II wherein the radicals $R_4$ and $R_5$ represent halogen for the remaining substituent positions given [see also: M. A. Davis et al., J.Med.Chem. 7, 88–94 (1964)].

Further starting products of formula II in which $R_5$ represents a methoxy radical in the 4-position can be produced in a corresponding manner from the 5-chloro-3-methoxy-5H-dibenzo[a,d]cycloheptene described in the literature (cp. U.S. Pat. No. 3,527,871) and the 3-methoxy-5H-dibenzo[a,d]cycloheptene-5-carbonitrile obtained therefrom. Further suitable starting materials are moreover the given (cp. loc. cit.) 3-trifluoromethyl-5H-dibenzo[a,d]cycloheptene-5-carbonitrile, 1-methyl- and 4-methyl-5H-dibenzo[a,d]cycloheptene-5-carbonitrile as well as 2-ethyl- and 3-tert-.butyl-5H-dibenzo[a,d]cycloheptene-5-carbonitrile, from which, by way of the carboxylic acids and carboxylic acid chlorides obtainable therefrom, are finally obtainable the correspondingly substituted starting products of formula II. Accessible in an analogous manner are the starting products of formula II wherein the radicals $R_4$ and $R_5$ represent trifluoromethyl, alkyl, alkoxy, hydroxy or esterified hydroxy groups for the remaining substituent positions. In the production of starting products of this type with esterified hydroxy groups, it can be advantageous to perform the esterification of the hydroxy groups corresponding to the meaning of $R_4$ and $R_5$ at a chosen stage during the production of the starting materials; a preferred alternative within the scope of the present invention consists in the esterification of such hydroxy groups at a reaction stage chosen to suitably fit in with the course of the reaction during the carrying out of the claimed processes according to the invention.

Further starting materials of the general formula II wherein Z represents the radical

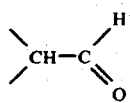

are obtainable from the known 1,1a,6,10b-tetrahydro-1,6-methano-dibenzo[a,e]cyclopropa[c]cyclohepten-11-one by reaction with, e.g., methoxymethyl-triphenylphosphonium chloride in the presence of strong alkali, e.g., sodium hydride, in an inert solvent such as, for instance, dimethylsulphoxide, in a temperature range of 20° to 70°C, preferably at 20°, then at 50°C by way of a Wittig-reaction, and subsequent hydrolysis, e.g., with conc. hydrochloric acid in a suitable solvent such as methanol or tetrahydrofuran. Further starting materials of this type which are characterised by the meanings of the substituents $R_4$ and $R_5$ can be produced in an analogous manner.

Starting materials of the general formula IV which are required for the second process can be produced, for example, as follows: 1,1a,6,10b-tetrahydro-1,6-methano-dibenzo[a,e]cyclopropa[c]cyclohepten-11-one is reacted in the presence of zinc chips activated with iodine with N,N-dimethyl-bromoacetamide in an inert solvent, e.g., absolute benzene, to obtain N,N-dimethyl-11-hydroxy-1,1a,6,10-tetrahydro-1,6-methano-dibenzo[a,e]cyclopropa[c]cycloheptene-11-acetamide. Further starting materials of this type which are characterised by the meanings of the substituents $R_4$ and $R_5$ can be produced in an analogous manner.

The starting materials of formula V which are required for the third process according to the invention can be produced, for example, as follows: 1,1a,6,10b-tetrahydro-1,6-methano-dibenzo[a,e]cyclopropa[c]cyclohepten-11-one in a suitable inert solvent such as, e.g., dimethylsulphoxide, is added to a reaction solution prepared from trimethylsulphoxoniumiodide and sodium hydride in dimethylsulphoxide, whereby there is obtained by way of a Wittig-reaction, after processing, spiro [1,1a,6,10b-tetrahydro-1,6-methano-dibenzo[a,e]cyclopropa[c]cyclohepzene-11,2'-oxirane]. Further starting materials of this type which are characterised by the meanings of the substituents $R_4$ and $R_5$ can be obtained, in principle, in the same manner.

The starting materials of the general formula VI which are required for the fifth process according to the invention are in some cases known from the literature. Thus, for example, a compound of the general formula VI wherein A represents the direct bond is produced by reduction of 1,1a,6,10b-tetrahydro-1,6-methano-dibenzo[a,e]cyclopropy[c]cycloheptene-11-one with sodium borohydride in methanol, whereby the secondary alcohol corresponding to the general formula VI is obtained [cp. V. Ioan, M. Popovici et al.: Tetrahedron Letters 38, 3383–3386 (1965)]. The corresponding sulphonic acid ester is obtained therefrom by reaction with a sulphonyl halide, e.g., methanesulphonyl chloride or p-toluenesulphonyl chloride, in pyridine. Further starting products of this type which combine the substitution characteristics given by the substituents $R_4$ and $R_5$ can be produced, in principle, in the same manner.

Further starting materials embraced by the general formula VI are obtainable by the reduction of a compound of the general formula II in which Z represents the radical

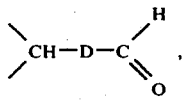

wherein D stands for the methylene or the ethylene radical or the ethylidene radical, the production of which as starting material for the first process was described in connection with this process, e.g., with sodium borohydride in methanol to the primary alcohol, whereby a compound of the general formula VI wherein A represents the ethylene radical or the trimethylene radical is obtained. The conversion of such a compound into a reactive ester, e.g., into the chloride, can be performed by reaction with thionyl chloride in the presence of absence of an inert solvent such as, for instance, benzene. Further compounds of this type which are characterised by the nature and position of the substituents $R_4$ and $R_5$ can be, in principle, obtained in the same manner.

Further starting materials embraced by the general formula VI can be produced from a compound corresponding to the general formula V by a process in which anhydrous hydrogen chloride, preferably dissolved in an inert anhydrous solvent such as benzene, is added with opening of the oxirane ring, as a result of which there is obtained a compound of the general formula VI wherein $R_1$ is hydroxyl, and the radical A is bound to chlorine and hence present as a reactive ester, namely as chloride.

Further substances of this type characterised by the nature and position of the substituents $R_4$ and $R_5$ can be produced in an essentially analogous manner.

The present invention relates also to such modifications of the described processes and of their preliminary stages whereby a process is interrupted at some stage, or whereby a compound occurring as an intermediate at some stage is used as the starting material and the uncompleted steps performed, or whereby a starting material is formed under the reaction conditions, or is optionally employed in the form of a salt. If the required starting substances are optically active, then both the racemates and the isolated antipodes can be used, or in the case of diastereomeric compounds either mixtures of racemates or specific racemates, or likewise isolated antipodes. Such starting substances too can optionally be used in the form of salts.

Where final materials are obtained as racemates or mixtures of racemates, these can be, within the scope of the present invention, optionally separated and split up into their antipodes.

The compounds of the general formula I obtained by the processes according to the invention are optionally converted, in the usual manner, into their addition salts with inorganic and organic acids. The following, for example, are used for salt formation: hydrochloric acid, hydrobromic acid, sulphuric acid, phosphoric acid, perchloric acid, methanesulphonic acid, ethanesulphonic acid or citric acid, preferably in the presence of a solvent such as, e.g., acetone, methanol, ethanol or ether, or mixtures thereof.

The compounds of the general formula I and the corresponding, pharmaceutically acceptable acid addition salts are preferably administered orally or rectally. The daily doses vary between 0.10 and 10 mg/kg for warm-blooded animals. Suitable dosage units, such as dragees, tablets or suppositories, preferably contain 0.5 – 50 mg of an active substance according to the invention, i.e. of a compound of the general formula I or of a pharmaceutically acceptable acid addition salt of these substances. The said dosage units are produced by combination of the active substance with solid pulverulent carriers such as lactose, saccharose, sorbitol, mannitol; starches such as potato starch, maize starch or amylopectin, also laminaria powder or citrus pulp powder; cellulose derivatives or gelatine, optionally with the addition of lubricants such as magnesium or calcium stearate or polyethylene glycols, to form tablets or dragee cores. The last-mentioned are coated, for example, with concentrated sugar solutions which may also contain, e.g., gum arabic, talcum and/or titanium dioxide, or with a lacquer dissolved in readily volatile organic solvents or mixtures of solvents. Dyestuffs can be added to these coatings, e.g., for identification of the various dosage amounts. Further suitable oral dosage units are hard gelatine capsules, as well as soft closed capsules made from gelatine and a softener such as glycerin. The former contain the active substance preferably as a granulate in admixture with lubricants such as talcum or magnesium stearate, and optionally stabilisers such as sodium metabisulphite or ascorbic acid.

The following directions further illustrate the production of tablets, dragees and suppositories:

a. An amount of 50.0 g of N,N-dimethyl-11-hydroxy-1,1a,6,10b-tetrahydro-1,6-methano-dibenzo[a,e]cyclopropa[c]cycloheptene-11ethylamine-hydrochloride is mixed with 500 g of lactose and 292 g of potato starch; the mixture is moistened with an alcoholic solution of 8 g of gelatine, and granulated through a sieve. After the drying of the granulate, 60 g of potato starch, 60 g of talcum, 10 g of magnesium stearate and 20 g of highly dispersed silicon dioxide are mixed in, and the mixture subsequently passed out to form 10,000 tablets each weighing 105 mg and each containing 5 mg of active substance; the tablets can optionally be provided with grooves to give a more precise adjustment of the dosage amount.

b. An amount of 2.5 g of N,N-dimethyl-1,1a,6,10b-tetrahydro-1,6-methano-dibenzo[a,e]cyclopropa[c]cycloheptene-11-amine-fumarate is well mixed with 16 g of maize starch and 6 g of highly dispersed silicon dioxide. The mixture is moistened with a solution of 2 g of stearic acid, 6 g of ethylcellulose and 6 g of stearin in ca. 70 ml of isopropyl alcohol, and granulated through a sieve III (Ph.Helv. V). The granulate is dried for ca. 14 hours and subsequently passed through sieve III-IIIa. It is then mixed with 16 g of maize starch, 16 g of talcum and 2 g of magnesium stearate, and the mixture pressed out to form 1000 dragee cores. These are coated with a concentrated syrup of 2 g of lacca, 7.5 g of gum arabic, 0.15 g of dyestuff, 2 g of highly dispersed silicon dioxide, 25 g of talcum and 53.35 g of sugar, and subsequently dried. The obtained dragees each weight 162.5 mg and each contain 2.5 mg of active substance.

c. 10.0 g of N-methyl-1,1a,6,10b-tetrahydro-1,6-methano-dibenzo[a,e]cyclopropa[c]cycloheptene-11-aminehydrochloride and 1990 g of finely ground suppository foundation substance (e.g. cocoa butter) are thoroughly mixed and then melted. From the melt, maintained homogeneous by stirring, are poured 1000 suppositories each weighing 2 g and each containing 10 mg of active substance.

d. An amount of 25.0 g of N,N-dimethyl-11-hydroxy-1,1a,6,10b-tetrahydro-1,6-methano-dibenzo[a,e]cyclopropa[c]cycloheptene-11-ethylamine-hydrochloride is dissolved in 1 litre of di-distilled, pyrogen-free water, and the solution filled into 1000 ampoules and these then sterilised. An ampoule contains a 2.5% solution of 25 mg of active substance.

It is likewise possible to use, as active substance for tablets, dragees, suppositories and injectionsolutions, the same amounts of N-methyl-1,1a,6,10b-tetrahydro-1,6-methano-dibenzo[a,e]cyclopropa[c]cycloheptene-11-methylamine-maleate or of 4-(11-hydroxy-1,1a,6,10b-tetrahydro-1,6-methano-dibenzo[a,e]cyclopropa[c]cyclohepten-11-yl)-1-methyl-piperidinehydrochloride.

The following examples further illustrate the production of the new compounds of the general formula I as well as of starting materials not hitherto known; the examples are, however, in no way intended to limit the scope of the invention. The given temperatures are expressed in degrees Centigrade.

EXAMPLE 1

An amount of 11.6 g (0.05 mole) of 1,1a,6,10b-tetrahydro-1,6-methano-dibenzo[a,e]cyclopropa[c]cyclohepten-11-one [V. Ioan, M. Popovici et al.: Tetrahedron Letters 38, 3383 (1965)] is dissolved in 200 ml of methanol, and 50 ml of a 33% solution of methylamine in ethanol added; the whole is heated, with stirring, to 35°, and subsequently stirred for a further hour at ca. 20°, whereby a thick precipitate is formed. There is then introduced into the reaction mixture with stirring, 3.8 g (0.1 mole) of sodium borohydride, with the temperature being maintained at 20° by cooling. The reaction mixture is subsequently stirred for one hour at 20° and then briefly refluxed. After cooling, the reaction mixture is completely concentrated in a waterjet vacuum. The residue is distributed between water and ether, and the ethereal phase extracted with 2N hydrochloric acid. The combined acidified extracts are rendered alkaline with concentrated ammonia and extracted with ether; the combined ether extracts are washed with water, dried over sodium sulphate and concentrated in a waterjet vacuum to obtain N-methyl-1,1a,6,10-tetrahydro-1,6-methano-dibenzo[a,e]cyclopropa[c]cycloheptene-11-amine; M.P. 142°–143°.

The hydrochloride prepared therefrom with ethereal hydrochloric acid in chloroform in recrystallised from methanol/acetone; M.P. 256°–258°.

EXAMPLE 2 a. Analogously to Example 1 there is obtained, from 12.3 g (0.05 mole) of 1,1a,6,10b-tetrahydro-1,6-methano-dibenzo[a,e]cyclopropa[c]cycloheptene-11-carboxaldehyde: N-methyl-1,1a,6,10b-tetrahydro-1,6-methano-dibenzo[a,e]cyclopropa[c]cycloheptene-11-methylamine; M.P. 65°–73°.

The maleate (1:1) prepared therefrom with maleic acid crystallises from methanol/ether; M.P. 147°–148°.

The 1,1a,6,10b-tetrahydro-1,6-methano-dibenzo[a.e]cyclopropa[c]cycloheptene-11-carboxaldehyde used as starting product is produced as follows:

b. 23.2 g (0.1 mole) of 1,1a,6,10b-tetrahydro-1,6-methano-dibenzo[a,e]cyclopropa[c]cyclohepten-11-one and 68.5 g (0.2 mole) of methoxymethyl-triphenylphosphonium chloride are dissolved in 300 ml of abs. dimethylsulphoxide; an addition is then made at ca. 20° to 8.75 g (0.2 mole) of a 55% suspension of sodium hydride in paraffin. There is formed a red solution with the evolution of hydrogen. After 30 minutes, the reaction mixture is heated to 50° and stirred for 15 hours at this temperature. After cooling, the reaction mixture is poured on 1000 ml of ice water and extracted with ether. The ether solution is washed repeatedly with water, dried over sodium sulphate and concentrated in a water-jet vacuum to obtain 52 g of the crude reaction product consisting of a mixture of the desired vinyl ether with triphenylphosphine oxide. This mixture is dissolved in benzene/petroleum ether (1:1), and chomatographed on ca. 150 g of silica gel. The fractions eluted with benzene/petroleum ether mixtures (1:1), then (1:2) and finally with pure benzene are crystallised, after removal of the solvent by evaporation, from benzene/petroleum ether to obtain pure 11-methoxymethylene-1,1a,6,10b-tetrahydro-1,6-methano-dibenzo[a,e]cyclopropa[c]cycloheptene; M.P. 139°–141°.

c. An amount of 13.0 g (0.5 mole) of 11-methoxymethylene-1,1a,6,10b-tetrahydro-1,6-methano-dibenzo [a,e]cyclopropa[c]cycloheptene is dissolved in 200 ml of methanol; an addition is made at 50° of 20 ml of conc. hydrochloric acid, and the whole stirred at this temperature for 15 minutes. The reaction mixture is then completely concentrated in a water-jet vacuum, the residue dissolved in 300 ml of tetrahydrofuran, and the solution stirred with 30 ml of 2N sulphuric acid for 3 hours at 50° under nitrogen. It is subsequently fully concentrated in a water-jet vacuum; the residue is distributed between water and ether, the ethereal phase washed neutral with water, dried over sodium sulphate and concentrated in a water-jet vacuum to obtain 1,1a,6,10b-tetrahydro-1,6-methano-dibenzo[a,e]cycloppropa[c]cycloheptene-11-carboxaldehyde in the form of colourless oil.

EXAMPLE 3

An amount of 464 mb (2mMoles) of 1,1a,6,10b-tetrahydro-1,6-methano-dibenzo[a,e]cyclopropa[c]cyclohepten-11-one is dissolved in 15 ml of a 15% solution of ammonia in methanol, and the solution allowed to stand in a closed flask for 48 hours at 20°. An addition is then made at ca. 20°, with stirring, of 152 mg of sodium borohydride. After 30 minutes, the reaction mixture is briefly refluxed and again cooled. Processing is carried out analogously to Example 1 to obtain 1,1a,6,10b-tetrahydro-1,6-methano-dibenzo[a,e]cyclopropa[c]cycloheptene-11-amine; M.P. 126°–127°.

EXAMPLE 4

An amount of 7.4 g (0.03 mole) of N-methyl-1,1a,6,10b-tetrahydro-1,6-methano-dibenzo[a,e]cyclopropa[c]cycloheptene-11-amine is dissolved in 12 ml of ice-cold 100% formic acid; an addition is then made of 14 g of 37% formaldehyde solution and the whole refluxed for 15 hours. The reaction mixture is cooled and 35 ml of 2N hydrochloric acid added; the mixture is subsequently completely concentrated in a water-jet vacuum. The residue is distributed between water and ether, the aqueous phase rendered alkaline with concentrated ammonia and extracted with ether. The combined ether extracts are washed with water, dried over sodium sulfate and concentrated in a water-jet vacuum to obtain N,N-dimethyl-1,11,6,10b-tetrahydro-1,6-methano-dibenzo[a,e]cyclopropa[c]cycloheptene-11-amine; M.P. 100°–104°.

The fumarate (1:1) prepared therefrom with fumaric acid crystallises from methanol/ether; M.P. 208°–210°.

EXAMPLE 5

There is obtained analogously to Example 4, from 7.8 g (0.03 mole) of N-methyl-1,1a,6,10b-tetrahydro-1,6-methano-dibenzo[a,e]cyclopropa[c]cycloheptene-11-methylamine obtained according to Example 2: N,N-dimethyl-1,1a,6,10b-tetrahydro-1,6-methano-dibenzo[a,e]cyclopropa[c]cycloheptene-11-methylamine; M.P. 60°–63°.

The hydrochloride prepared therefrom with ethereal hydrochloric acid in chloroform solution is recrystallised from methanol/ether; M.P. 247°–249°.

EXAMPLE 6 a. An amount of 6.2 g (0.025 mole) of spiro[1-,1a,6,10b-tetrahydro-1,6-methano-dibenzo[a,e]cyclopropa [c]cycloheptene-11,2′-oxirane]is stirred with 60 ml of a 35% solution of dimethylamine in ethanol for 15 hours at ca. 20°. The reaction mixture is subsequently completely concentrated in a water-jet vacuum, the residue taken up in ether, and the ethereal solution extracted with 2N hydrochloric acid. The combined acidified extracts are made alkaline with concentrated ammonia and extracted with ether. The combined ethereal extracts are washed with water, dried over sodium sulphate and concentrated in a water-jet vacuum to obtain N,N-dimethyl-11-hydroxy-1,1a,6,10b-tetrahydro-1,6-methano-dibenzo[a,e]cyclopropa[c]cycloheptene-11-methylamine; M.P. 100°–105°.

The fumarate (1:1) prepared therefrom with fumaric acid crystallises from methanol/ether; M.P. 210°–211°.

The spiro[1,1a,6,10b-tetrahydro-1,6-methano-dibenzo [a,e]cyclopropa[c]cycloheptene-11,2′-oxirane]used as starting material is produced as follows:

b. An amount of 19.8 g (0.09 mole) of trimethylsulphoxonium iodide is dissolved in 180 ml of abs. dimethylsulphoxide and the solution placed into the reaction vessel. There is then introduced under nitrogen 2.16 g (0.09 mole) of sodium hydride; the reaction mixture is subsequently stirred for 30 minutes at room temperatue; a clear solution is thus formed with the evolution of hydrogen. There is then added dropwise, in the course of 30 minutes, a solution of 17.4 g (0.075 mole) of 1,1a,6,10b-tetrahydro-1,6-methano-dibenzo[a,e]cyclopropa[c cyclohepten-11-one in 75 ml of abs. dimethylsulphoxide; the reaction mixture is afterwards stirred for a further 30 minutes; it is then poured on 1000 ml of ice water and extracted with ether. The combined ethereal phases are repeatedly washed with water, dried over sodium sulphate and concentrated in a water-jet vacuum. The residue crystallises from ether/petroleum ether to yield spira[1,1a,6,10b-tetrahydro-1,6-methano-dibenzo[a,e]cyclopropa[c]cycloheptene-11,2′-oxirane]; M.P. 160°–162°.

EXAMPLE 7

There is obtained analogously to Example 6, from the same amount of starting material and 60 ml of a 30% solution of isopropylamine in ethanol: N-isopropyl-11-hydroxy-1,1a,6,10b-tetrahydro-1,6-methano-dibenzo[a,e]cyclopropa[c]cycloheptene-11-methylamine; M.P. 124°.

The methanesulphonate prepared therefrom with methanesulphonic acid crystallised from methanol/ether; M.P. 207°–208°.

EXAMPLE 8 a. An amount of 2.28 g (0.06 mole) of lithium aluminium hydride is dissolved in 150 ml of abs. ether and the solution placed into a reaction vessel. An addition is then made dropwise at 25° within 60 minutes, with stirring, of a solution of 9.6 g (0.03 mole) of N,N-dimethyl-11-hydroxy-1,1a,6,10b-tetrahydro-1,6-methano-dibenzo[a,e]cyclopropa[c]cycloheptene-11-acetamide in 300 ml of abs. tetrahydrofuran. The reaction mixture is subsequently stirred at 25° for 15 hours. Successive additions are then slowly made dropwise, with vigorous stirring, of 2.3 ml of water, 2.3 ml of 15% sodium hydroxide solution and 6.9 ml of water. The formed precipitate is filtered off under suction, washed with ether, and the filtrate exhaustingly extracted with 2N hydrochloric acid. The combined acidified extracts are rendered alkaline with conc. ammonia and extracted with ether. The combined ether extracts are washed with water, dried over sodium sulphate and concentrated under a water-jet vacuum. The residue obtained is N,N-dimethyl-11 -hydroxy-1,1a, 6,10b-tetrahydro-1,6-methano-dibenzo[a,e]cyclopropa[c] cycloheptene-11-ethylamine in the form of colourless oil.

The hydrochloride prepared therefrom in acetone solution with ethereal hydrochloric acid is recrystallised from methanol/ether; M.P. 245°–246°.

The N,N-dimethyl-11-hydroxy-1,1a,6,10b-tetrahydro-1,6-methano-dibenzo[a,e]cyclopropa[c]cycloheptene-11-acetamide used as starting product is produced as follows:

b. An amount of 3.6 g (0.055 mole) of zinc chips and a trace of iodine are placed into a dry reaction vessel; additions are then made of 2 ml of a solution of 7.0 g (0.03 mole) of 1,1a,6,10b-tetrahydro-1,6-methano-dibenzo[a,e]cyclopropa[c]cyclohepten-11-one and 7.1 g (0.039 mole) of N,N-dimethyl-bromoacetamide in 50 ml of abs. benzene, and the whole is refluxed while stirring is maintained; the remainder of the benzene solution is added dropwise in the course of 30 minutes and refluxing subsequently performed for a further hour. After cooling, the reaction mixture is decomposed with 6 ml of glacial acetic acid and 6 ml of methanol. The formed organic precipitate is taken into solution by the addition of benzene and zinc residues still present are filtered off. The benzene solution is washed with 2N acetic acid, then with 2N sodium bicarbonate solution and finally with water; it is then dried over sodium sulphate and concentrated in a water-jet vacuum. The residue crystallises from benzene/petroleum ether to yield N,N-dimethyl-11-hydroxy-1,1a,6,10b-tetrahydro-1,6-methano-dibenzo[a,e] cyclopropa[c]cycloheptene-11-acetamide; M.P. 203°–204°.

EXAMPLE 9

In a reaction vessel, 1.95 g (0.08 mole) of magnesium chips under dry nitrogen is covered with 12 ml of abs. tetrahydrofuran, and corroded with a trace of iodine and 0.1 ml of ethylbromide. While stirring is maintained, 10.7 g (0.08 mole) of 1-methyl-4-chloropiperidine, dissolved in 30 ml of abs. tetrahydrofuran, is added dropwise at 60° in such a manner that the reaction mixture remains boiling. Refluxing is performed for a further 30 minutes until all the magnesium is dissolved. To this Grignard solution cooled to 5° is then added dropwise at 5-10° in the course of 30 minutes, with stirring, 4.46 g (0.02 mole) of 1,1a,6,10b-tetrahydro-1,6-methano-dibenzo[a,e]cyclopropa[c]cyclohepten-11-one dissolved in 20 ml of abs. tetrahydrofuran. The reaction mixture is subsequently heated to ca. 20° and then stirred into 350 ml of a 3% ammonium chloride solution. The reaction product precipitated in crystalline form is filtered off with suction, washed with water and dried in a water-jet vacuum at ca. 50° to obtain 4-(11-hydroxy-1,1a,6,10b-tetrahydro-1,6-methano-dibenzo[a,e]cyclopropa[c]cyclohepten-11-yl)-1-methyl-piperidine; M.P. 239°–242°.

The hydrochloride prepared therefrom in chloroform solution with ethereal hydrochloric acid is recrystallised from methanol/ether; M.P. 285°–286°.

What we claim is:

1. An antidepressive and stimulating pharmaceutical composition comprising an antidepressively and stimulating effective amount of a compound having the formula I

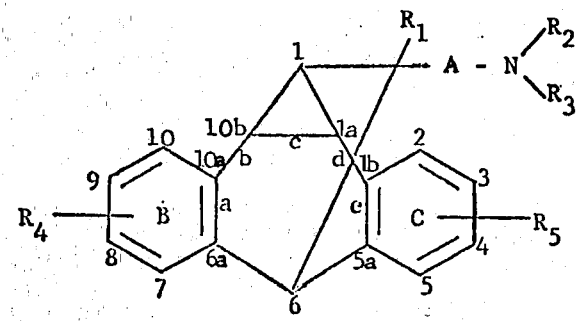

(I)

wherein $R_1$ represents hydrogen or the hydroxy group, $R_2$ and $R_3$ represent hydrogen or alkyl groups having 1 to 3 carbon atoms, $R_4$ and $R_5$ represent hydrogen, and A represents the direct bond, an alkylene radical having 1 to 3 carbon atoms, or together with

the 1-methyl-4-piperidyl radical, or one of its pharmaceutically acceptable addition salts with an inorganic or organic acid, together with a diluent and/or carrier.

2. The composition of claim 1, comprising a compound of the formula I, wherein $R_1$, $R_4$ and $R_5$ represent hydrogen, and $R_2$, $R_3$ and A have the meanings defined in claim 1, or of one of its pharmaceutically acceptable addition salts with an inorganic or organic acid, together with a diluent and/or carrier.

3. The composition of claim 1, comprising compound of the formula I, wherein $R_1$ is the hydroxy group, $R_2$, $R_3$ and A have the meanings defined in claim 1, and $R_4$ and $R_5$ stand for hydrogen, or of one of its pharmaceutically acceptable addition salts with an inorganic or organic acid, together with a diluent and/or carrier.

4. The composition of claim 1, comprising N,N-dimethyl-11-hydroxy-1,1a,6,10b-tetrahydro-1,6-methano-dibenzo[a,e]cyclopropa[c]cycloheptene-11-ethylamine-hydrochloride, together with a diluent and/or carrier.

5. The method of producing an antidepressive effect in a warm-blooded animal which comprises administering to said mammal in antidepressively effective amount of a compound of the formula I given in claim 1, wherein $R_1$, $R_2$, $R_3$, $R_4$, $R_5$ and A have the meanings defined in claim 1 or of one of its pharmaceutically acceptable addition salts with an inorganic or organic acid.

* * * * *